(12) United States Patent
Sanchez et al.

(10) Patent No.: US 10,188,400 B2
(45) Date of Patent: Jan. 29, 2019

(54) INTRALUMINAL OCCLUDING CATHETER

(71) Applicants: Jaime Eduardo Sanchez, Tampa, FL (US); Michael Eric Dolberg, Miramar, FL (US); Sowsan Heidar Rasheid, Wesley Chapel, FL (US)

(72) Inventors: Jaime Eduardo Sanchez, Tampa, FL (US); Michael Eric Dolberg, Miramar, FL (US); Sowsan Heidar Rasheid, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/468,698

(22) Filed: Aug. 26, 2014

(65) Prior Publication Data

US 2015/0065995 A1    Mar. 5, 2015

Related U.S. Application Data

(60) Provisional application No. 61/870,566, filed on Aug. 27, 213.

(51) Int. Cl.
*A61M 25/10* (2013.01)
*A61B 17/12* (2006.01)
(Continued)

(52) U.S. Cl.
CPC .. *A61B 17/12136* (2013.01); *A61B 17/12099* (2013.01); *A61M 25/10* (2013.01);
(Continued)

(58) Field of Classification Search
CPC .. A61M 2025/0079; A61M 2025/0078; A61M 2025/1052; A61M 25/1025;
(Continued)

(56) References Cited

U.S. PATENT DOCUMENTS 3,948,270 A * 4/1976 Hasson ................. A61M 25/01
604/515
4,231,365 A * 11/1980 Scarberry ............. A61M 16/04
128/207.15
(Continued)

OTHER PUBLICATIONS

Buess G, Theiss R, Gunther M, Hutterer F, Pichlmaier H. Transanal endoscopic microsurgery. Leber Magen Darm 1985; 15:271-279.
(Continued)

*Primary Examiner* — Jenna Zhang
(74) *Attorney, Agent, or Firm* — Michele L. Lawson; Smith & Hopen, P.A.

(57) ABSTRACT

An intraluminal occluding catheter and method for preventing the loss of gas insufflation from a physiological lumen during a medical procedure is presented. The intraluminal occluding catheter is generally comprised of a catheter shaft having a flexible balloon affixed on a distal intraluminal end and a plurality of independent channels extending through the catheter shaft from the external proximal end to the distal intraluminal end. Once inserted into a physiological lumen such as the bowel, the intraluminal occluding catheter controls the loss of insufflation proximally thereby improving the safety and efficiency of TAMIS as well as allowing for more controlled gas exchange to clear smoke or vapor.

13 Claims, 11 Drawing Sheets

(51) Int. Cl.
A61M 25/00 (2006.01)
A61M 39/08 (2006.01)
A61M 39/10 (2006.01)
A61B 17/00 (2006.01)

(52) U.S. Cl.
CPC .............. *A61B 2017/00818* (2013.01); *A61M 2025/0079* (2013.01); *A61M 2025/1052* (2013.01); *A61M 2039/082* (2013.01); *A61M 2039/1083* (2013.01); *A61M 2202/02* (2013.01); *A61M 2210/1064* (2013.01); *A61M 2210/1067* (2013.01)

(58) Field of Classification Search
CPC .......... A61M 25/0075; A61M 2202/02; A61M 2025/0004; A61M 2025/0036; A61M 2025/0037; A61M 2025/004; A61M 25/0026; A61M 25/0028; A61M 25/0029; A61M 25/003; A61M 2039/082; A61M 2039/1083; A61B 17/12136; A61B 2017/00818; A61B 17/12099
See application file for complete search history.

(56) References Cited

U.S. PATENT DOCUMENTS

| | | | | |
|---|---|---|---|---|
| 4,328,806 A | * | 5/1982 | Cooper | A61M 25/0009 600/374 |
| 4,407,304 A | * | 10/1983 | Lieber | A61M 25/0009 607/122 |
| 4,584,998 A | * | 4/1986 | McGrail | A61M 16/04 128/207.15 |
| 5,429,597 A | | 7/1995 | DeMello et al. | |
| 5,499,625 A | * | 3/1996 | Frass | A61M 16/04 128/200.26 |
| 6,582,395 B1 | * | 6/2003 | Burkett | A61M 25/04 604/910 |
| 8,211,128 B1 | * | 7/2012 | Facundus | A61B 17/1114 128/898 |
| 8,409,166 B2 | | 4/2013 | Wiener et al. | |
| 2002/0045852 A1 | * | 4/2002 | Saab | A61F 7/123 604/96.01 |
| 2005/0043649 A1 | * | 2/2005 | Urie | A61B 5/037 600/561 |
| 2007/0106247 A1 | * | 5/2007 | Burnett | A61F 7/12 604/508 |
| 2011/0160648 A1 | * | 6/2011 | Hoey | A61B 18/04 604/26 |
| 2011/0263974 A1 | * | 10/2011 | Wiener | A61B 17/3417 600/431 |

OTHER PUBLICATIONS

Buess G, Kipfmuller K, Hack D, Grussner R, Heintz A, Junginger T. Technique of transanal endoscopic microsurgery. Surg Endosc 1988; 2:71-75.

Buess G. Review: transanal endoscopic microsurgery (TEM). J R Coll Surg Edinb 1993; 38:239-245.

Atallah S, Albert M, Larach S. Transanal minimally invasive surgery: a giant leap forward. Surg Endosc 2010; 24:2200-2205.

Walensi M, Kaser SA, Theodorou P, Bassotti G, Cathomas G, Maurer CA. Transanal endoscopic microsurgery (TEM) facilitated by video-assistance and anal insertion of a single-incision laparoscopic surgery (SILS®)-port: preliminary experience. World J Surg 2014; 38:505-511.

Khoo RE. Transanal excision of a rectal adenoma using single-access laparoscopic port. Dis Colon Rectum 2010; 53:1078-1079.

Slack T, Wong S, Muhlmann M. Transanal minimally invasive surgery: an initial experience. ANZ J Surg 2014; 84:177-180.

Lee TG, Lee SJ. Transanal single-port microsurgery for rectal tumors: minimal invasive surgery under spinal anesthesia. Surg Endosc 2014; 28:271-280.

Barendse RM, Doornebosch PG, Bemelman WA, Fockens P, Dekker E, de Graaf EJ. Transanal employment of single access ports is feasible for rectal surgery. Ann Surg 2012; 256:1030-1033.

Hayashi S, Takayama T, Yamagata M, Matsuda M, Masuda H. Single-incision laparoscopic surgery used to perform transanal endoscopic microsurgery (SILSTEM) for T1 rectal cancer under spinal anesthesia: report of a case. Surg Today 2013; 43:325-328.

Canda AE, Terzi C, Sagol O, Sarioglu S, Obuz F, Fuzun M. Transanal single-port access microsurgery (TSPAM). Surg Laparosc Endosc Percutan Tech 2012; 22:349-353.

Sehgal R, Cahill RA. Advanced laparoscopic surgery for colorectal disease: NOTES/NOSE or single port? Best Pract Res Clin Gastroenterol. 2014; 28:81-96.

Atallah SB, Albert MR, deBeche-Adams TH, Larach SW. Robotic transanal minimally invasive surgery in a cadaveric model. Tech Coloproctol 2011; 15:461-464.

Rimonda R, Arezzo A, Arolfo S, Salvai A, Morino M. TransAnal Minimally Invasive Surgery (TAMIS) with SILS™ port versus Transanal Endoscopic Microsurgery (TEM): a comparative experimental study. Surg Endosc 2013; 27:3762-3768.

Atallah S, Albert M, Debeche-Adams T, Larach S. Transanal minimally invasive surgery (TAMIS): applications beyond local excision. Tech Coloproctol 2013; 17:239-243.

Bak Y, Merriam M, Neff M, Berg DA. Novel approach to rectal foreign body extraction. JSLS 2013; 17:342-345.

Bardakcioglu O. Robotic transanal access surgery. Surg Endosc 2013; 27:1407-1409.

Mirnezami AH, Mirnezami R, Venkatasubramaniam AK, Chandrakumaran K, Cecil TD, Moran BJ. Robotic colorectal surgery: hype or new hope? A systematic review of robotics in colorectal surgery. Colorectal Dis 2010; 12:1084-1093.

Hompes R, Rauh SM, Hagen ME, Mortensen NJ. Preclinical cadaveric study of transanal endoscopic da Vinci® surgery. Br J Surg 2012; 99:1144-1148.

Atallah S, Nassif G, Polavarapu H, et al. Robotic-assisted transanal surgery for total mesorectal excision (RATS-TME): a description of a novel surgical approach with video demonstration. Tech Coloproctol 2013; 17:441-447.

McLemore EC, Coker A, Jacobsen G, Talamini MA, Horgan S. eTAMIS: endoscopic visualization for transanal minimally invasive surgery. Surg Endosc 2013; 27:1842-1845.

Takahashi H, Yamasaki M, Hirota M, et al. Automatic smoke evacuation in laparoscopic surgery: a simplified method for objective evaluation. Surg Endosc 2013; 27:2980-2987.

English Translation of Buess G, Theiss R, Gunther M, Hutterer F, Pichlmaier H. Transanal endoscopic microsurgery. Leber Magen Darm 1985; 15:271-279.

International Preliminary Report on Patentability issued by the International Bureau dated Mar. 10, 2016 for corresponding international patent application No. PCT/US2014/052785.

* cited by examiner

INTRALUMINAL OCCLUDING CATHETER

CROSS REFERENCE TO RELATED APPLICATIONS

This application is a nonprovisional of and claims priority to U.S. Provisional Patent Application No. 61/870,566, entitled "Intraluminal Bowel Occluding Catheter", filed Aug. 27, 2013, the entire contents of which is herein incorporated into this disclosure.

FIELD OF INVENTION

This invention relates to catheters. More specifically, the invention relates to an intraluminal catheter capable of preventing the loss of insufflation when performing laparoendoscopic procedures.

BACKGROUND OF THE INVENTION

Transanal excision of rectal neoplasms has until recently been essentially limited to tumors of the low rectum. However, transanal endoscopic microsurgery (TEM) allowed access to higher rectal tumors through the use of specialized equipment in order to avoid unnecessary proctectomy (Buess G, Theiss R, Gunther M, Hutterer F, Pichlmaier H. Transanal endoscopic microsurgery. Leber Magen Darm 1985; 15:271-279; Buess G, Kipfmuller K, Hack D, Grussner R, Heintz A, Junginger T. Technique of transanal endoscopic microsurgery. Surg Endosc 1988; 2:71-75; Buess G. Review: transanal endoscopic microsurgery (TEM). J R Coll Surg Edinb 1993; 38:239-245).

A more recent advancement hybridizing the concept of TEM with single-incision laparoscopy has led to the creation of transanal minimally invasive surgery (TAMIS) (Atallah S, Albert M, Larach S. Transanal minimally invasive surgery: a giant leap forward. Surg Endosc 2010; 24:2200-2205). This innovative approach is seeing increasing popularity as a safe, feasible and cost-effective alternative to TEM, providing the benefits at reduced cost with a possibly shorter learning curve (Walensi M, Kaser S A, Theodorou P, Bassotti G, Cathomas G, Maurer C A. Transanal endoscopic microsurgery (TEM) facilitated by video-assistance and anal insertion of a single-incision laparoscopic surgery (SILS®)-port: preliminary experience. World J Surg 2014; 38:505-511; Khoo R E. Transanal excision of a rectal adenoma using single-access laparoscopic port. Dis Colon Rectum 2010; 53:1078-1079; Slack T, Wong S, Muhlmann M. Transanal minimally invasive surgery: an initial experience. ANZ J Surg 2014; 84:177-180; Lee T G, Lee S J. Transanal single-port microsurgery for rectal tumors: minimal invasive surgery under spinal anesthesia. Surg Endosc 2014; 28:271-280).

TAMIS is generally easier to set up, and provides a viewing quality comparable to traditional laparoscopy. Additionally, single-incision laparoscopic ports allow greater instrument maneuverability, and have been shown to cause less anorectal trauma (Walensi M, Kaser S A, Theodorou P, Bassotti G, Cathomas G, Maurer C A. Transanal endoscopic microsurgery (TEM) facilitated by video-assistance and anal insertion of a single-incision laparoscopic surgery (SILS®)-port: preliminary experience. World J Surg 2014; 38:505-511; Slack T, Wong S, Muhlmann M. Transanal minimally invasive surgery: an initial experience. ANZ J Surg 2014; 84:177-180; Barendse R M, Doornebosch P G, Bemelman W A, Fockens P, Dekker E, de Graaf E J. Transanal employment of single access ports is feasible for rectal surgery. Ann Surg 2012; 256:1030-1033; Hayashi S, Takayama T, Yamagata M, Matsuda M, Masuda H. Single-incision laparoscopic surgery used to perform transanal endoscopic microsurgery (SILSTEM) for T1 rectal cancer under spinal anesthesia: report of a case. Surg Today 2013; 43:325-328; Canda A E, Terzi C, Sagol O, Sarioglu S, Obuz F, Fuzun M. Transanal single-port access microsurgery (TSPAM). Surg Laparosc Endosc Percutan Tech 2012; 22:349-353).

Despite its multiple advantages over traditional transanal excision techniques, TAMIS does have its limitations. Single port procedures can be expensive, and have an inherent tendency for instrument clash (Sehgal R, Cahill R A. Advanced laparoscopic surgery for colorectal disease: NOTES/NOSE or single port? Best Pract Res Clin Gastroenterol. 2014; 28:81-96). Rectal insufflation can be lost through the trocar seals when torque forces on the instruments are extreme, or it can also be lost passively into the proximal bowel (Atallah S B, Albert M R, deBeche-Adams T H, Larach S W. Robotic transanal minimally invasive surgery in a cadaveric model. Tech Coloproctol 2011; 15:461-464). Additionally, the cost-effectiveness of TAMIS may be limited by the need for an assistant surgeon to manage the camera (Barendse R M, Doornebosch P G, Bemelman W A, Fockens P, Dekker E, de Graaf E J. Transanal employment of single access ports is feasible for rectal surgery. Ann Surg 2012; 256:1030-1033; Rimonda R, Arezzo A, Arolfo S, Salvai A, Morino M. TransAnal Minimally Invasive Surgery (TAMIS) with SILS™ port versus Transanal Endoscopic Microsurgery (TEM): a comparative experimental study. Surg Endosc 2013; 27:3762-3768). TAMIS has also been reported to have longer operative times than TEM (; Rimonda R, Arezzo A, Arolfo S, Salvai A, Morino M. TransAnal Minimally Invasive Surgery (TAMIS) with SILS™ port versus Transanal Endoscopic Microsurgery (TEM): a comparative experimental study. Surg Endosc 2013; 27:3762-3768).

Colon and rectal surgeons have commonly encountered some major time-consuming and technical obstacles to performing safe and efficient TAMIS procedures such as fluctuation of pneumorectum as insufflation gas escapes proximally into the bowel, causing repeated collapse of the rectal lumen as well as dense smoke created from electrocautery devices obscuring the visual field.

The instant invention alleviates the above obstacles encountered during TAMIS procedures and in addition can be used for any sort of endoscopic procedure to ensure a clear visual field during the procedure.

SUMMARY OF INVENTION

The intraluminal occluding catheter presented herein addresses the loss of gas insufflation from the lumen of a body cavity such as the bowel when performing medical procedures. When gas is used to insufflate the bowel, in order to distend the walls and provide sufficient working space, it is often lost from the area of interest due to passage within the lumen causing collapse of the working space. This has become a particularly important problem with the development of advanced techniques that allow complex procedures to be performed within the lumen of the bowel instead of more morbid abdominal or pelvic operations.

Specifically, this invention is particularly useful to prevent the loss of insufflation with either gas or fluid when performing endoscopic procedures in a body cavity such as in the rectum or colon as with a colonoscopy as well as when performing laparoendoscopic procedures within the rectum such as the transanal minimally invasive surgery (TAMIS) technique. The invention can also be used in other body cavities such as the bowel, esophagus, stomach, colon and small intestine.

The intraluminal occluding catheter is generally comprised of a catheter shaft, a flexible balloon affixed at one end of the catheter shaft and a plurality of independent channels that extend the length of the catheter shaft and into the balloon. The catheter shaft may have an exterior surface; an interior surface defining an inner lumen; a distal section terminating at an intraluminal end; a plurality orifices disposed in the distal section of the catheter shaft; and a proximal section terminating at an external end. The flexible balloon may be affixed to the intraluminal end. Preferably the balloon is capable of conforming to a size and shape of a physiological lumen when filled with gas or fluid. The plurality of independent channels have proximal and distal ends and extend through the inner lumen of the catheter shaft with the distal end of each channel having an aperture disposed therein that may be positioned substantially in alignment with the corresponding orifice in the catheter shaft.

In some embodiments, the intraluminal occluding catheter may also have a flow control device positioned at the proximal end of each channel to open or occlude each channel. This flow control device may be a valve or stopcock.

In an alternative embodiment, an adapter is positioned between the flow control device and the proximal end of each channel.

The device may be further comprised of a sleeve attached to the external end of the catheter shaft with the plurality of independent channels extending through the sleeve and into the inner lumen of the catheter shaft.

Further, a removable wire may be inserted into one of the plurality of channels to provide rigidity when inserting the catheter into a patient.

A method of preventing the loss of gas insufflation in a physiological lumen during a medical procedure is also presented. The method comprises inserting the intraluminal occluding catheter into the physiological lumen, positioning the catheter so that it is proximal to the area having the medical procedure, inflating the balloon, performing the medical procedure, deflating the balloon and removing the catheter. If smoke or vapor is created during the medical procedure, it may be evacuated passively through one of the open channels or a smoke removal apparatus or system may be attached to one of the channels to remove the smoke/vapor to allow for a clear viewing field.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
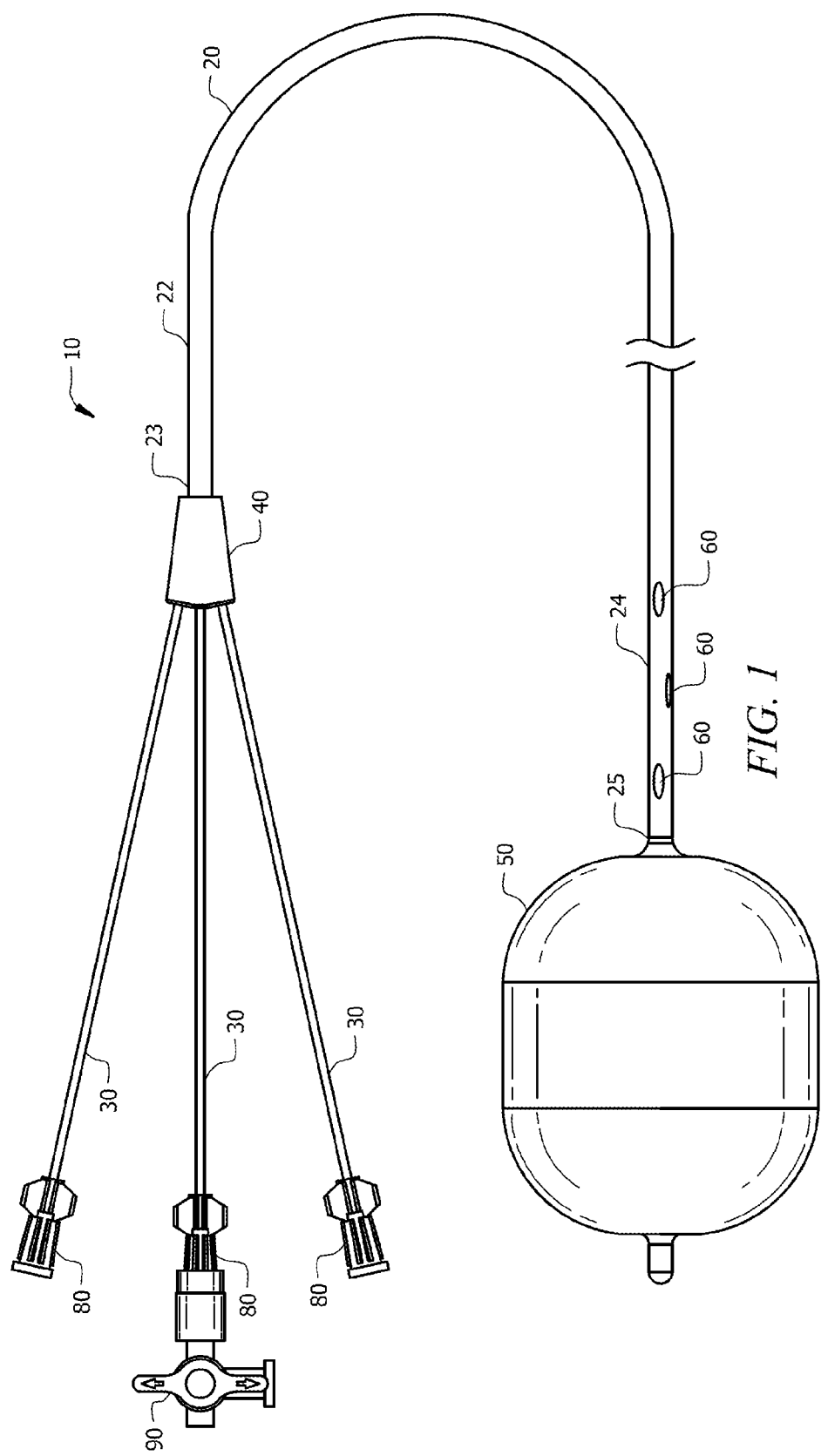
FIG. 1 is a perspective image of the intraluminal occluding catheter.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

As used in the specification and claims, the singular form "a", "an" and "the" include plural references unless the context clearly dictates otherwise.

"Substantially" as used herein refers to an amount greater than 50%. In an embodiment, "substantially" refers to a proportional relationship in which one element is largely aligned with or covers a large proportion of the surface of another element.

"Adapter" as used herein refers to a device which connects different parts of an apparatus, particularly an adapter allows one part of the apparatus to be coupled to an otherwise incompatible device or system. In the instant case, the adapter may be used to connect a channel with a flow control device or other device used in conjunction with the intraluminal occluding catheter described herein such as a smoke removal device, a light emitting device, an insufflator device, etc.

"Sleeve" as used herein refers to a single continuous structure with two open ends that fits over or around another structure. In the instant case, the plurality of channels are extended through one end of the sleeve and is used to gather the individual channels in a tighter space before they extend into the catheter shaft. At the opposite end, the sleeve fits around the external proximal end of the catheter shaft. In the figures the sleeve is funnel-shaped, however any shape is contemplated as long as the catheter shaft is capable of being attached to one end and all channels are capable of extending through the opposite end into the catheter shaft.

"A plurality" as used herein refers to at least two of the indicated components.

"Flow control device" as used herein refers to any device that is capable of regulating, directing or controlling the flow of a medium such as a gas, liquid, fluidized solid or powder into or out of a space by opening, closing or partially obstructing a passageway. Exemplary flow control devices that may be used in the instant invention include, but are not limited to, valves and stopcocks.

"Physiological lumen" as used herein refers to a cavity within a hollow organ in an animal, preferably a mammal, more preferably a human. Examples of physiological lumens include, but are not limited to, the bowel, stomach, intestines, and esophagus.

"Inflation" as used herein refers to filling the balloon of a catheter with gas or fluid.

"Insufflation" as used herein refers to the act of blowing something, such as a gas, powder or vapor, into a body cavity. In TAMIS, insufflation is continued throughout the procedure to ensure the bowel lumen remains open.

TAMIS is a versatile operative technique seeing increased usage not only for the local resection of rectal neoplasms, but in even more complex operations as well. It has been described for use in total mesorectal excision (TAMIS-TME) procedures, transanal completion proctectomies, ligation of rectal Dieulafoy's lesions, repair of rectourethral fistulas, and extraction of recto-sigmoid foreign bodies (Atallah S, Albert M, Debeche-Adams T, Larach S. Transanal minimally invasive surgery (TAMIS): applications beyond local excision. Tech Coloproctol 2013; 17:239-243; Bak Y, Merriam M, Neff M, Berg D A. Novel approach to rectal foreign body extraction. JSLS 2013; 17:342-345).

TAMIS is seeing major advancements in both technological and technical aspects. The advent of robotic TAMIS is one such innovation that may also improve the technique. For example, instrument clash while working in the tight confines of the rectum is a commonly encountered problem that may be reduced with the dexterity of the robot (Atallah S B, Albert M R, deBeche-Adams T H, Larach S W. Robotic transanal minimally invasive surgery in a cadaveric model. Tech Coloproctol 2011; 15:461-464; Bardakcioglu O. Robotic transanal access surgery. Surg Endosc 2013; 27:1407-1409; Mirnezami A H, Mirnezami R, Venkatasubramaniam A K, Chandrakumaran K, Cecil T D, Moran B J. Robotic colorectal surgery: hype or new hope? A systematic review of robotics in colorectal surgery. Colorectal Dis 2010; 12:1084-1093; Hompes R, Rauh S M, Hagen M E, Mortensen N J. Preclinical cadaveric study of transanal endoscopic da Vinci® surgery. Br J Surg 2012; 99:1144-1148). Additionally, the robot may also provide superior ergonomics and three-dimensional viewing (Atallah S, Nassif G, Polavarapu H, et al. Robotic-assisted transanal surgery for total mesorectal excision (RATS-TME): a description of a novel surgical approach with video demonstration. Tech Coloproctol 2013; 17:441-447). Endoscopic visualization for TAMIS (eTAMIS) is another advancement, found to minimize instrument collision and provide enhanced visual clarity (McLemore E C, Coker A, Jacobsen G, Talamini M A, Horgan S. eTAMIS: endoscopic visualization for transanal minimally invasive surgery. Surg Endosc 2013; 27:1842-1845).

With more widespread use, and as TAMIS progresses, it becomes increasingly important to find solutions to commonly encountered difficulties. Fluctuation of pneumorectum frequently obscures laparoscopic visualization, and may increase the risk of instrument collisions and accidental maneuvers. This can be is hazardous, as it may cause accidental lacerations, perforations, and thermal damage to the bowel.

Smoke produced by electrocautery is also a factor that limits visualization, causing loss of precision and time. Ultrasonic shears, in contrast, produce a low-temperature vaporization of biologic material rather than smoke (Takahashi H, Yamasaki M, Hirota M, et al. Automatic smoke evacuation in laparoscopic surgery: a simplified method for objective evaluation. Surg Endosc 2013; 27:2980-2987; Barrett W L, Garber S M. Surgical smoke: a review of the literature. Is this just a lot of hot air? Surg Endosc 2003; 17:979-987; Johnson G K, Robinson W S. Human immunodeficiency virus-1 (HIV-1) in the vapors of surgical power instruments. J Med Virol 1991; 33:47-50). Ultrasonic dissection compared to standard electrosurgery has also been found to cause significantly less intraoperative blood loss (140.8 mL vs 182.6 mL, $p=0.032$) (20. Morino M, Rimonda R, Allaix M E, Giraudo G, Garrone C. Ultrasonic versus standard electric dissection in laparoscopic colorectal surgery: a prospective randomized clinical trial Ann Surg 2005; 242:897-901). Of note however, both types of dissectors become heated during use, with the potential to cause thermal injury to the rectum if inadvertently applied to tissues, especially in the case of obscured visualization.

TAMIS Procedure

The patient is placed in lithotomy position and the rectum is irrigated as desired. The perineum is draped in a sterile fashion. Gentle digital dilation of the anus is performed, and a transanal, single-incision, laparoscopic port is introduced. Insufflation is achieved using carbon dioxide instead of air to facilitate resorption of retained gas and improve postoperative patient comfort. The rectal neoplasm is excised, and the resultant defect is repaired.

Maintenance of Pneumorectum

During conventional TAMIS procedures, there are considerable fluctuations in the degree of distention of the rectal lumen as well as collapse, which occur as gas escapes proximally into the colon. The frequency of this collapse depends on factors such as the angulation of rectosigmoid junction or the location of the rectal lesion where dissection is needed. To properly maintain pneumorectum (at the appropriate pressure of approximately 15-20 cm of water) throughout the operation, the inventors developed an intraluminal occluding catheter to prevent loss of insufflation proximally. Once a port is placed in the anus, the catheter is introduced through the port, and with the intraluminal end of the catheter placed proximal to the lesion or at the rectosigmoid junction. One channel is used for inflation of the balloon which is performed under direct visualization. Full occlusion of the lumen is assured by cessation of flow from the laparoscopic insufflator at an appropriate pressure. The use of this device in the bowel is known as balloon occlusive transanal minimally invasive surgery.

Electrocautery Smoke

The use of electrocautery during TAMIS can create a significant amount of thick smoke, which is not readily evacuated from within the confined space of the lumen, obscuring the visual field and slowing progress of the operation. As well, loss of visualization can be unsafe during the critical portion of the operation when dissection is occurring. Use of an ultrasonic dissector, which produces vapor as a byproduct, instead of smoke, leads to improved visualization. Although gas exchange is still necessary to clear the vapor from the field of view, the problem is more easily managed. The instant invention is capable of removing the smoke or vapor caused by electrosurgical devices by allowing passive flow through, or attaching a smoke removal system to the proximal end of one of the channels. The smoke or vapor is drawn through orifices in one channel of the catheter shaft, out of the viewing area, and up the channel once the smoke removal system is operated.

Figure 2:
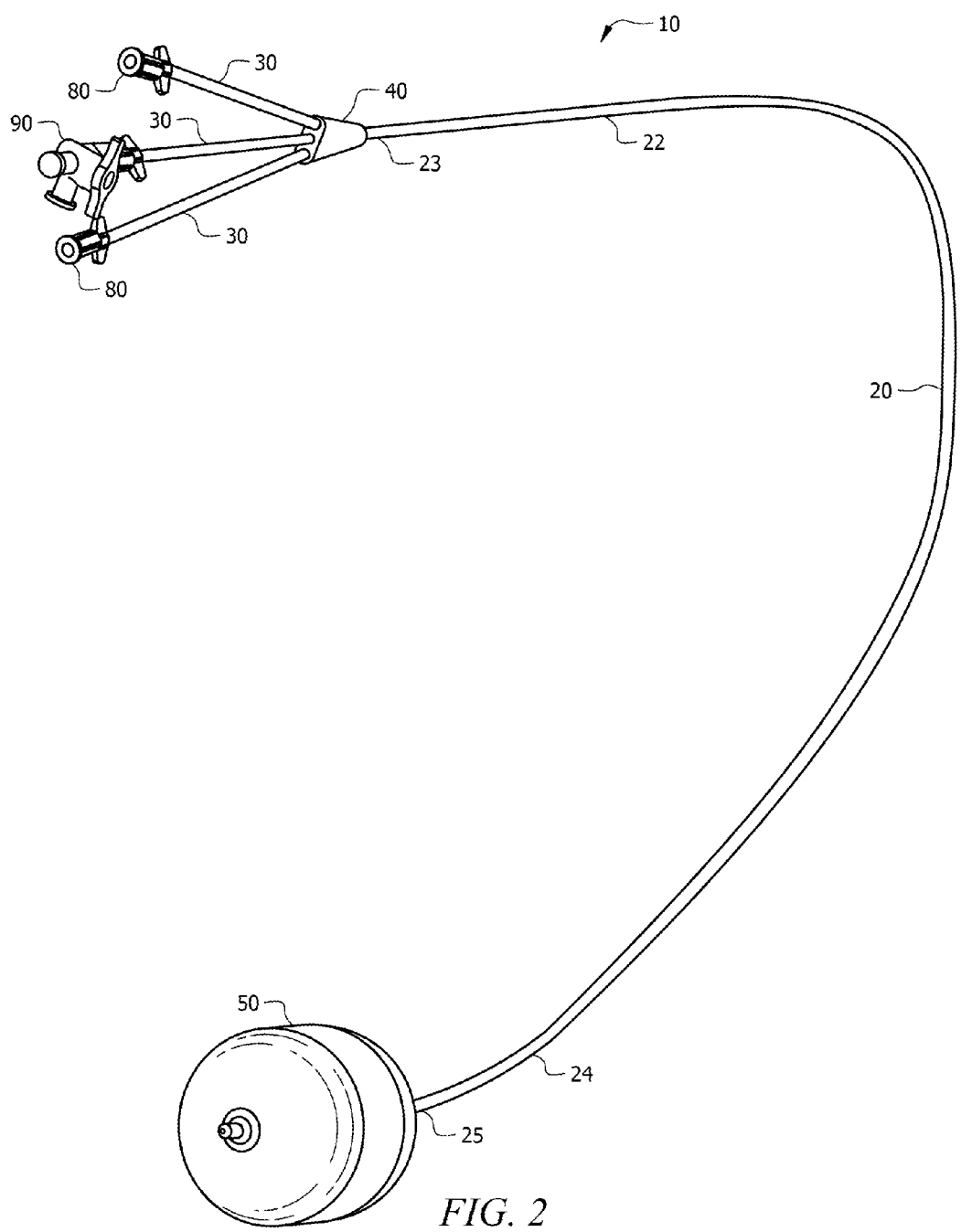
FIG. 2 is a perspective image of the intraluminal occluding catheter.

As illustrated in FIGS. 1 and 2, catheter 10 is generally composed of semi-rigid catheter shaft 20 having an exterior and interior surface which defines inner lumen 26 through which a plurality of separate and independent channels 30 extend. Catheter shaft 20 is composed of proximal section 22 which terminates at external end 23 and distal section 24 which terminates at intraluminal end 25. Channels 30 extend through inner lumen 26 of catheter shaft 20 from proximal section 22 to distal section 24 where flexible balloon 50 is affixed. Catheter shaft 20, and correspondingly channels 30, extend into inner lumen of balloon 50.

Figure 3:
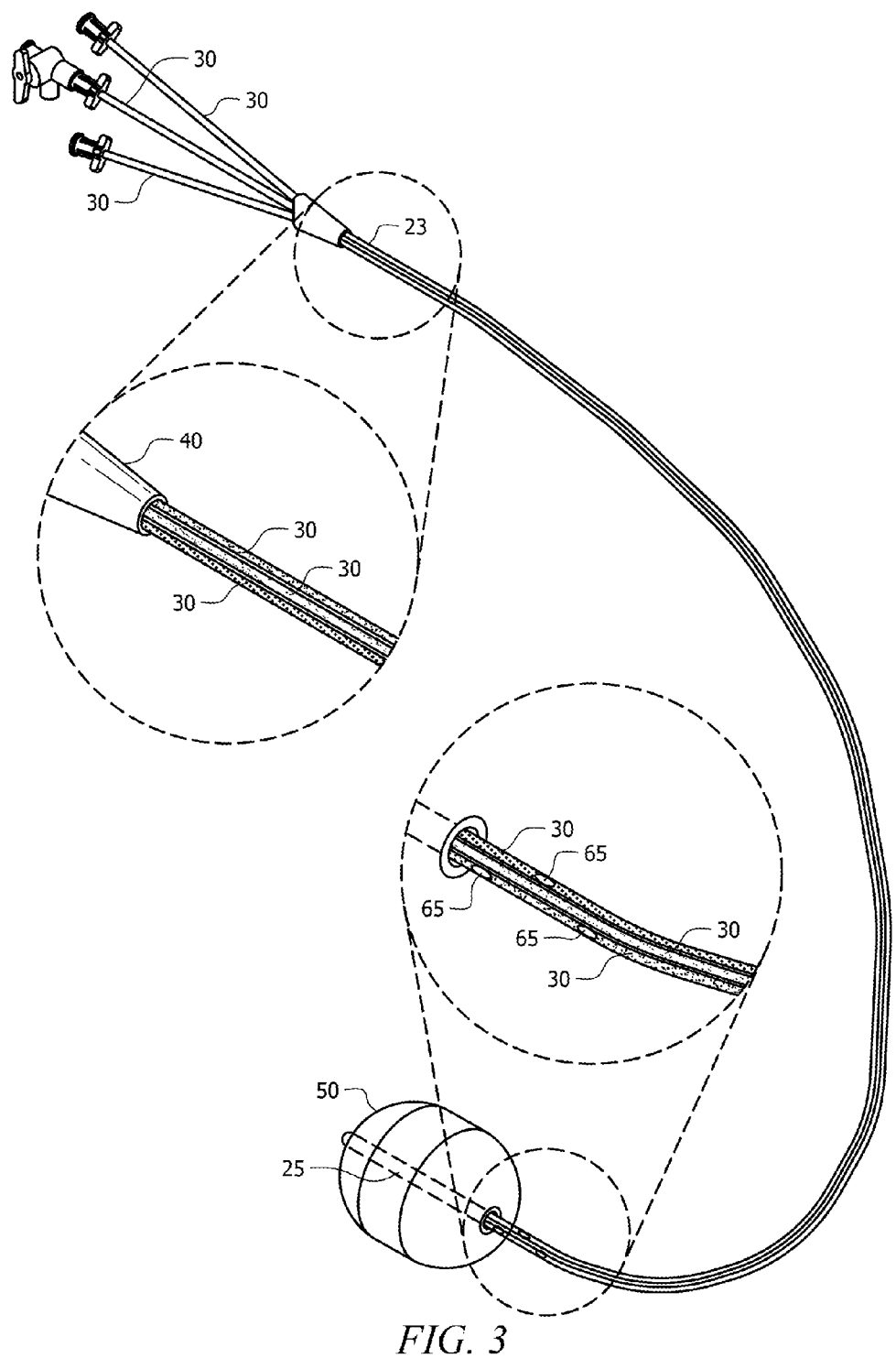
FIG. 3 is a magnified image of the proximal section of the catheter shaft illustrating the connection of the catheter shaft to the sleeve as well as the channels extending through the catheter shaft and the distal section of the catheter shaft illustrating the connection of the catheter shaft to the balloon as well as the orifices in the catheter shaft. As shown in the image, one channel has apertures at the distal end which is within the balloon to allow for inflation of the balloon. The other channels may have apertures outside the balloon. Apertures close to the balloon, but not within the balloon are used for evacuation of smoke, vapor and gas toward the balloon and thus away from the operative site. Apertures slightly farther from the balloon allow insufflation gas to enter the lumen of the bowel.

FIG. 3 is a transparent view of catheter 10. The proximal end (external end) of catheter 10 has multiple independent channels 30 that correspond to the individual internal channels 30 within inner lumen 22 of catheter shaft 20. As shown in the figure, channels 30 extend from proximal section 22 of catheter shaft 20 to distal section 24 of catheter shaft 20 to provide a plurality of separate independent channels within inner lumen 26 of catheter shaft 20. While the number of channels shown in the figures is three, the number of channels may vary as long as they are capable of fitting within the inner lumen of the catheter shaft. In some embodiments channels 30 may have apertures 65 positioned at distal end to allow for removal of smoke/vapor from the potential space. Apertures 65 located in the walls of each of channels 30 are substantially aligned with corresponding orifices 60 in catheter shaft 20. As shown in FIG. 3, one channel 30 has apertures 65 only within balloon 50 to allow for inflation of balloon 50. To inflate balloon 50, a syringe or other inflation device is attached to the proximal end of channel 30. A different channel 30 may have one or more apertures 65 near balloon 50, allowing for evacuation of smoke, vapor and gas toward balloon 50 and thus away from the camera and operative site. Another different channel 30 may have one or more apertures 65 slightly farther from balloon 50 to allow insufflation gas to enter the lumen of the bowel and push the smoke toward balloon 50 and away from the camera and operative site. Channels 30 may be used for various purposes according to the needs of the physician including, but not limited to, inflation of the balloon with gas; insufflation of gas or instillation of fluid into the lumen of the bowel; evacuation of gas, smoke or vapor from the lumen of the bowel; and internal lighting of the lumen.

Figure 4:
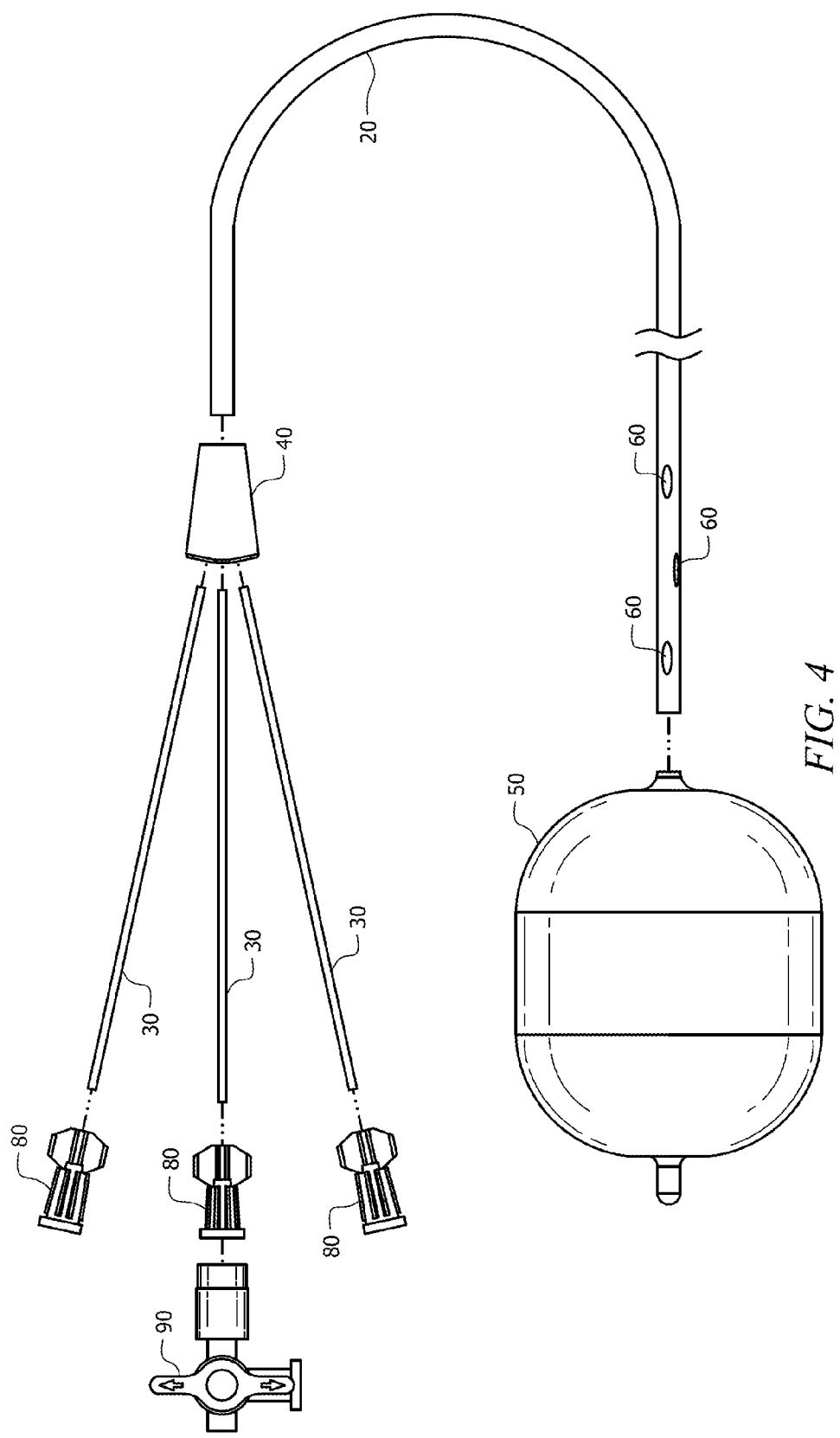
FIG. 4 is an exploded image of the intraluminal occluding catheter.

FIG. 4 is an exploded view of catheter 10. Adapter 80 is capable of attaching to proximal end of each channel 30. Flow control device 90 is shown as an example of a device that can be attached to adapter 80, however any device known in the art for use with catheters during endoscopic surgery may be attached to adapter 80. For example, instead of flow control device 90, a Plume-Away™ smoke evacuation system device may be attached to adapter 80 to remove smoke from the visual field; a light emitting device may be placed directly through adapter to further illuminate the visual field; or a fluid irrigation device may be attached to adapter 80 to irrigate the site. Additionally, flow control device 90 can be attached to adapter 80 and an additional device may then be attached to flow control device 90 so that the channel may be opened or closed according to the use of the device. For example, this device can be a smoke/vapor removal system described previously or an insufflator device to fill the bowel lumen with air or other gas. Channels 30 may be gathered and extend through sleeve 40 which can be attached to proximal section 22 of catheter shaft 20. Sleeve 40 allows channels 30 to be more easily inserted into proximal section 22 of catheter shaft 20. Balloon 50 is shown as attaching to distal section 24 of catheter shaft 20.

Figure 5:
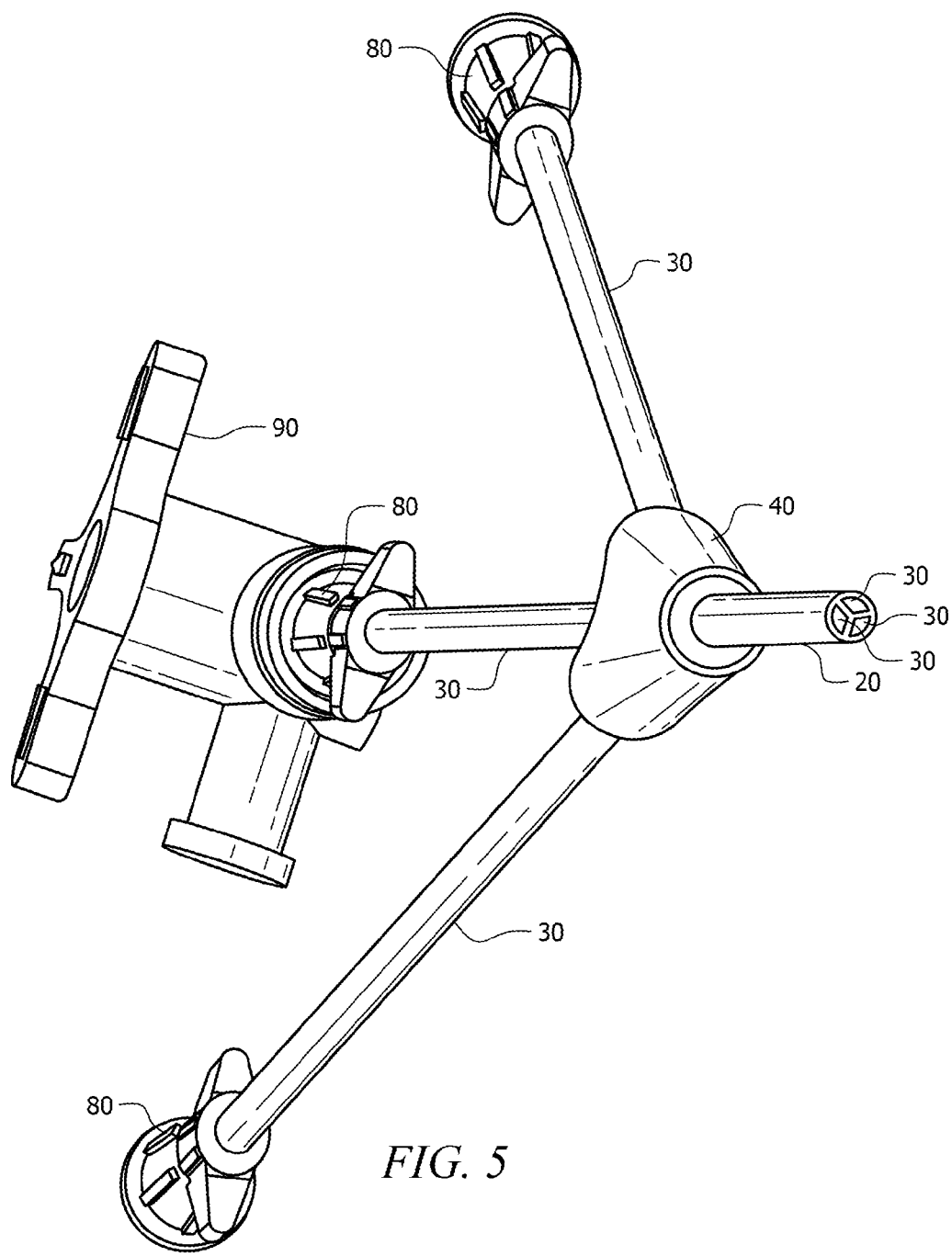
FIG. 5 is a perspective image of a portion of the proximal section of the intraluminal occluding catheter.
Figure 7:
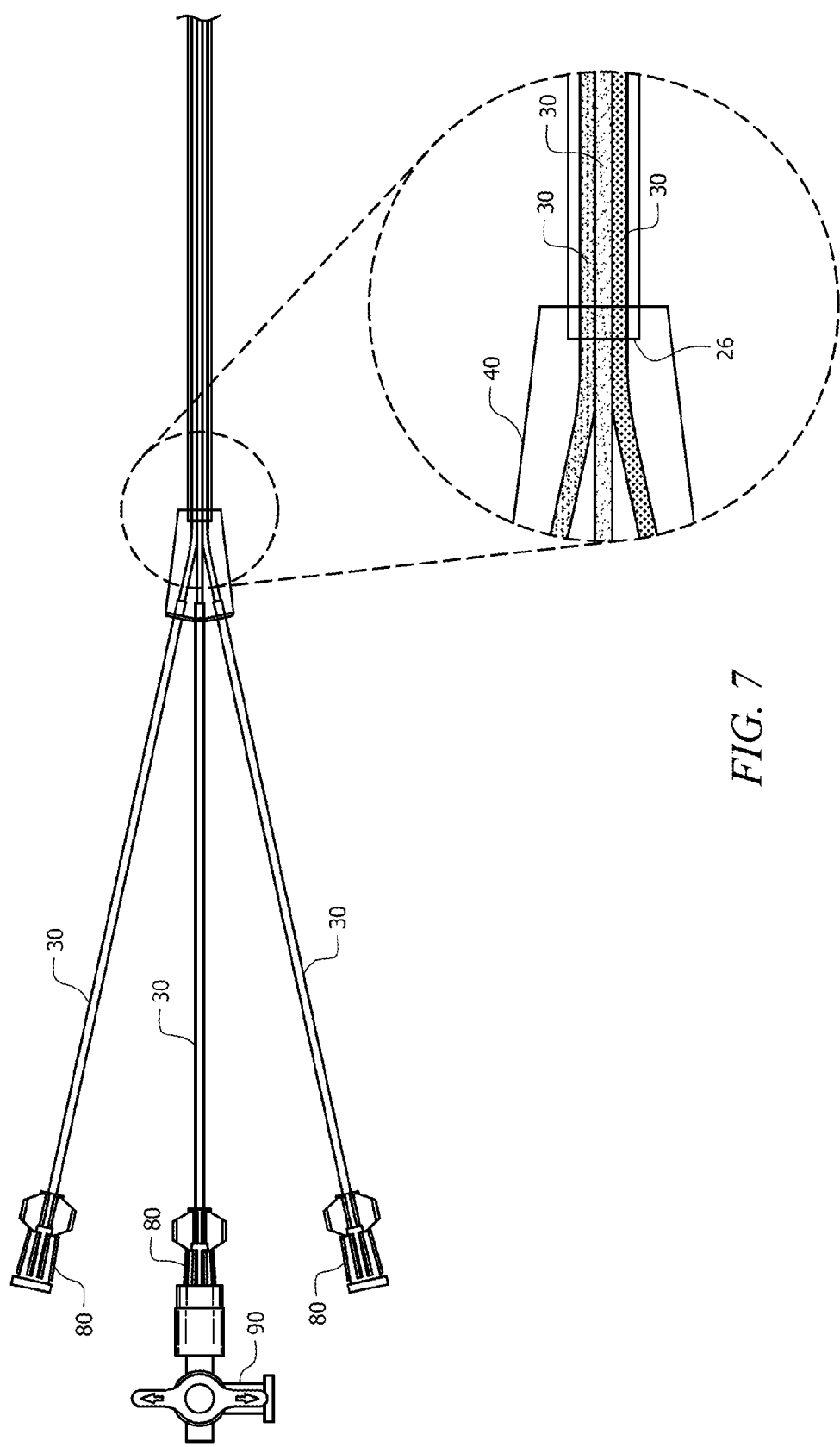
FIG. 7 is a transparent view of the sleeve showing the individual channels extending through sleeve and into catheter shaft.

FIG. 5 illustrates a cut-away section of proximal section 22 of catheter shaft 20 showing channels 30 extending through sleeve 40. FIG. 7 is a transparent view inside sleeve 40 and catheter shaft 20. As shown in the figures, channels 30 are gathered and positioned to extend through sleeve 40. Catheter shaft 20 is affixed to opposite end of sleeve 40 and channels 30 pass through sleeve 40 and into catheter shaft 20 to form a plurality of independent channels within inner lumen 26 of catheter shaft 20. The proximal end of each of channels 30 may have adapter 80 onto which flow control device 90 is connected. Flow control device 90 is capable of occluding or opening an individual channel 30. Adapters 80 are shown as attached to proximal end of channels 30 with flow control device 90 shown as attaching to adapter 80 of one channel 30. Adapter 80 may be any type of adapter known in the art to be used to attach a flow control device or other medical instrument. An example of such adapter includes, but is not limited to, a Luer Lock. Flow control device 90 may be any flow control device known in the art to be capable of opening or closing channel 30 such as a valve or stopcock.

Figure 6:
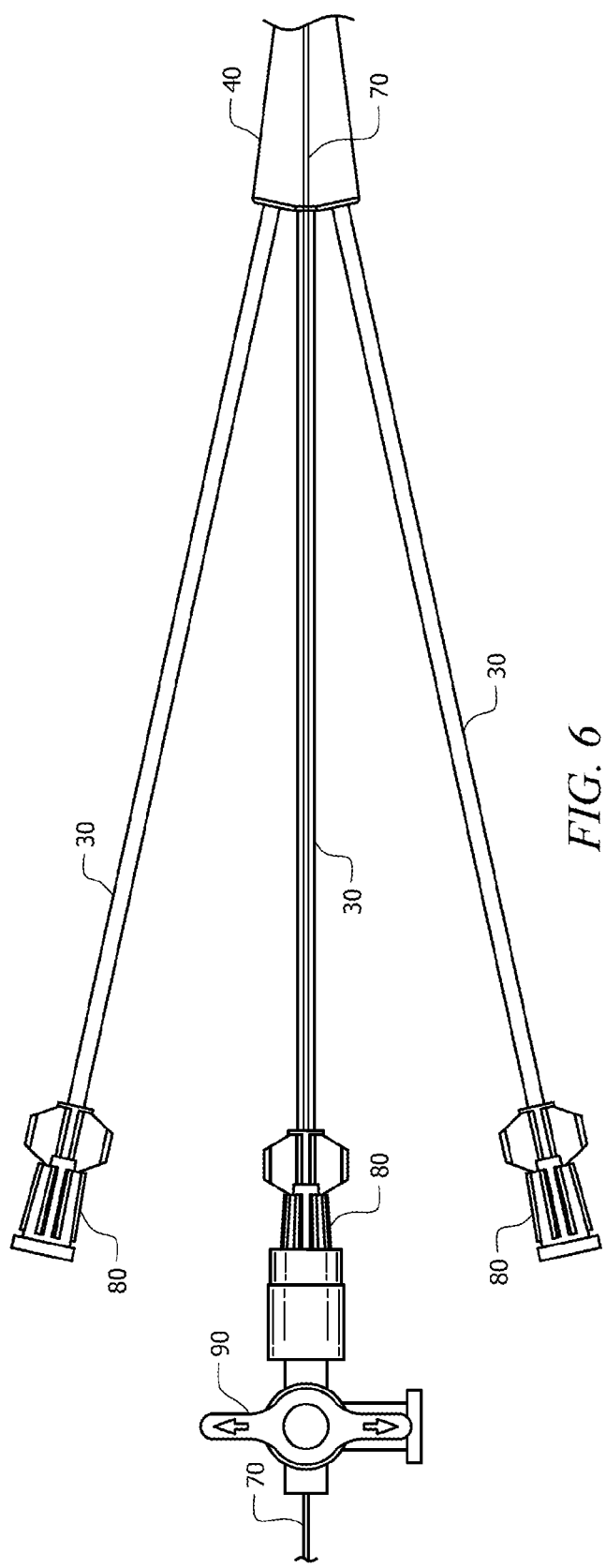
FIG. 6 is a front view of the proximal section of the intraluminal occluding catheter illustrating the wire extending through the middle channel.
Figure 10:
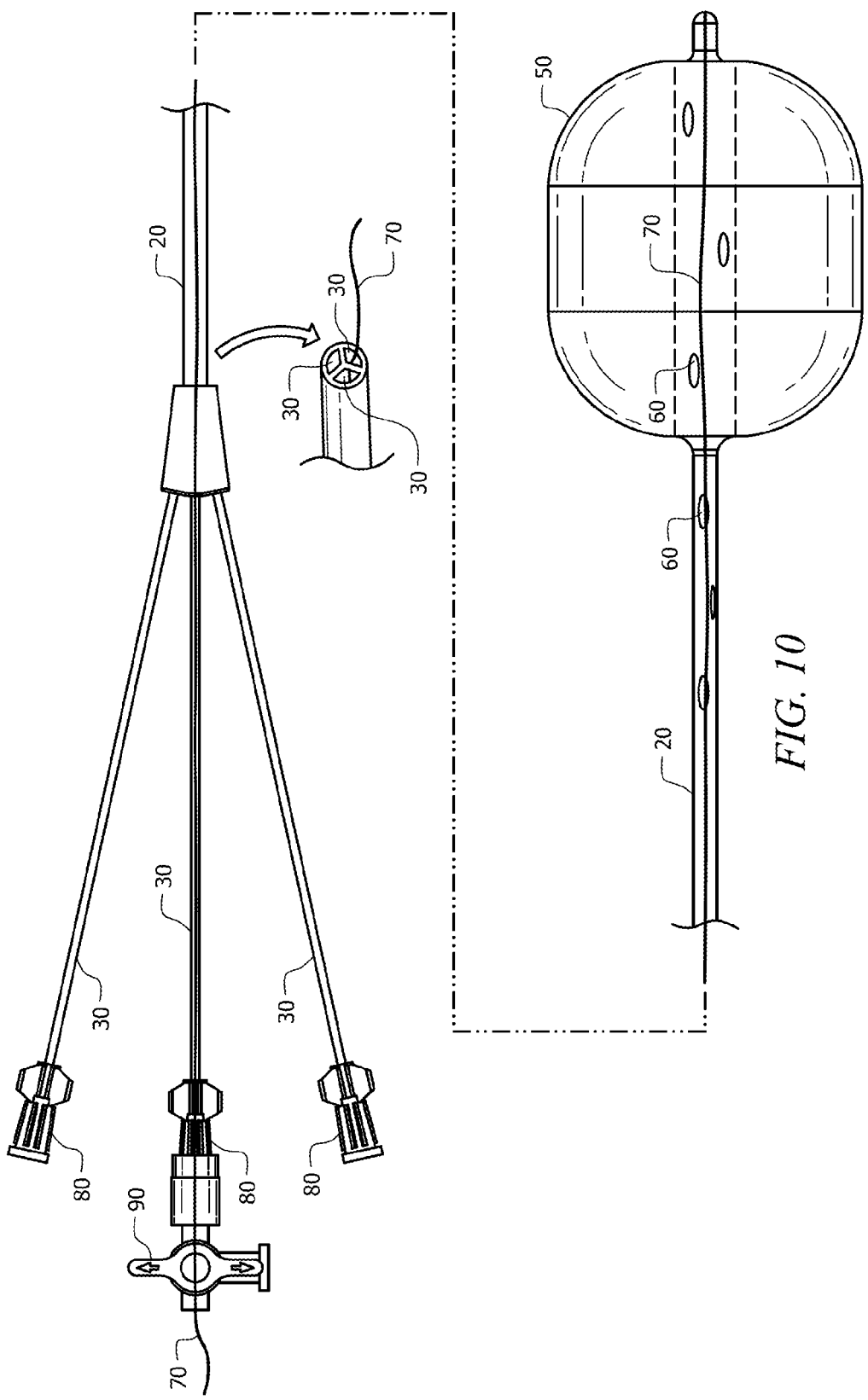
FIG. 10 is an exploded image showing a cross section of the catheter shaft with the individual channels extending therethrough.

As shown in FIGS. 6 and 10, one channel 30 may have removable wire 70 slideably disposed within inner lumen of channel 30. Wire 70 extends outwardly from proximal end of channel 30 and extends through inner lumen of channel 30 to distal end of channel 30 which is located in balloon 50. (FIG. 8) Wire 70 provides additional rigidity to catheter 10 and allows for catheter 10 to be more easily placed in the physiological lumen. Once catheter 10 is placed within the body of the patient, wire 70 may be easily removed allowing channel 30 to be used for another purpose such as inflation of balloon 50.

Figure 8:
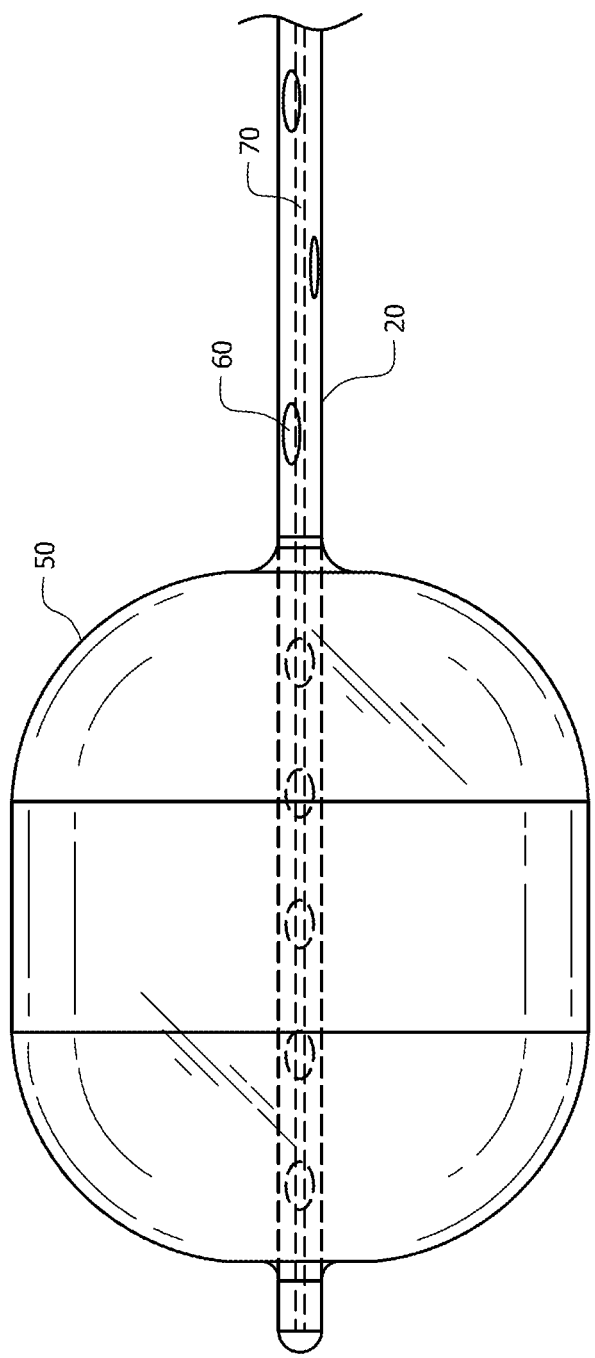
FIG. 8 is a front view of the distal section of the intraluminal occluding catheter showing the distal section of the catheter shaft extending into the balloon. Orifices are also shown in the catheter shaft.
Figure 9A:
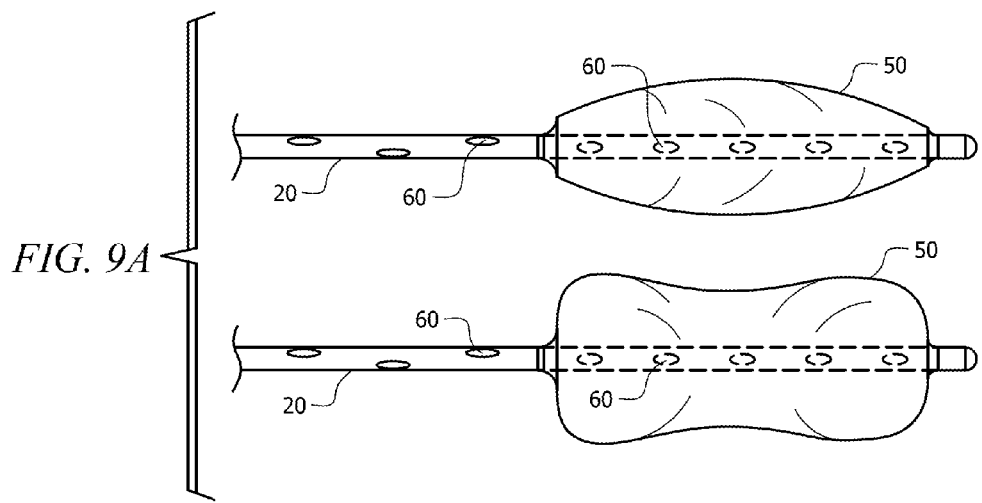
FIGS. 9A-B are a series of images depicting the balloon as attached to the catheter shaft. A) balloon deflated and B) balloon inflated. As shown in the image, the balloon can take any shape as long it is capable of conforming to the physiological lumen into which it is placed.
Figure 9B:
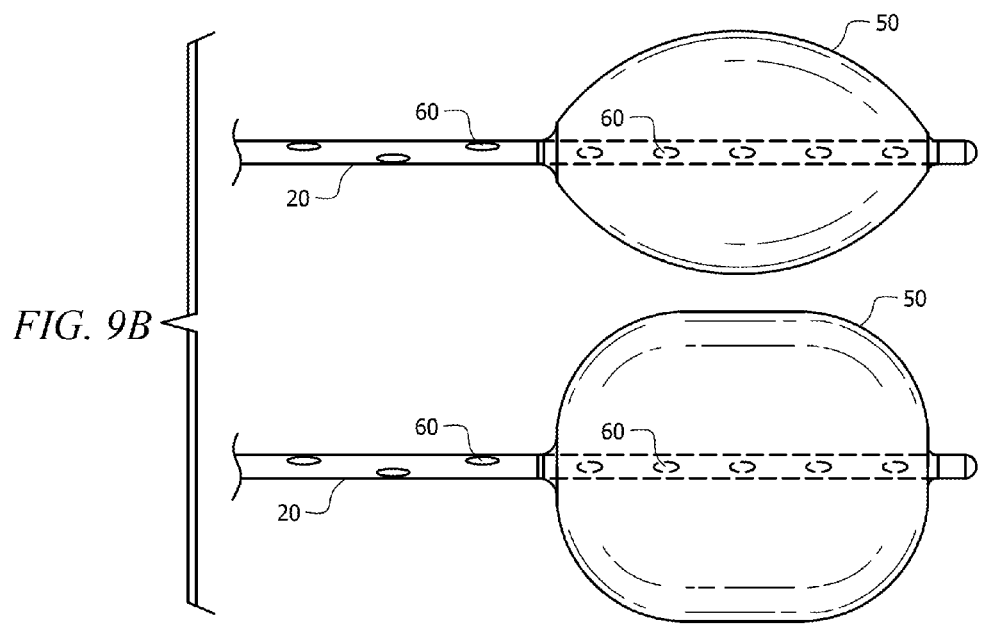

FIGS. 8 and 9 depict distal section 24 of catheter shaft 20 illustrating a plurality of orifices 60 disposed within distal section. Each orifice 60 in catheter shaft 20 corresponds to a similarly placed aperture 65 found in one or more channels 30. Corresponding orifice 60 and aperture 65 allows for inflation/deflation of balloon 50, insufflation of gas into the physiologic lumen, removal of smoke/vapor from the potential space, etc. FIG. 9A depicts balloon 50 in a deflated state while FIG. 9B depicts balloon in an inflated state. FIGS. 9A and B also illustrate that any shape of balloon may be used as long as it is capable of conforming to the physiological lumen.

Balloon 50 is affixed to distal section 24 of catheter 20 by any means known to those in the art including, but not limited to, heat bonding or adhesive. Intraluminal end 25 of catheter 20 extends through the inner lumen of balloon 50 with proximal waist of balloon 50 being secured to exterior surface of distal section 24 of catheter shaft 28. Balloon 50 is a flexible balloon capable of conforming to the size and shape of the bowel lumen, or any other lumen/cavity such as the esophagus, small intestine, colon or stomach, when filled with gas or fluid. Any type of balloon may be used as long as it has the ability to expand in size with inflation while attached to the catheter and completely occlude the given cavity, in this example the proximal rectal lumen, without injury. An example of such balloon for use in the rectum is an anal manometry balloon.

Figure 11:
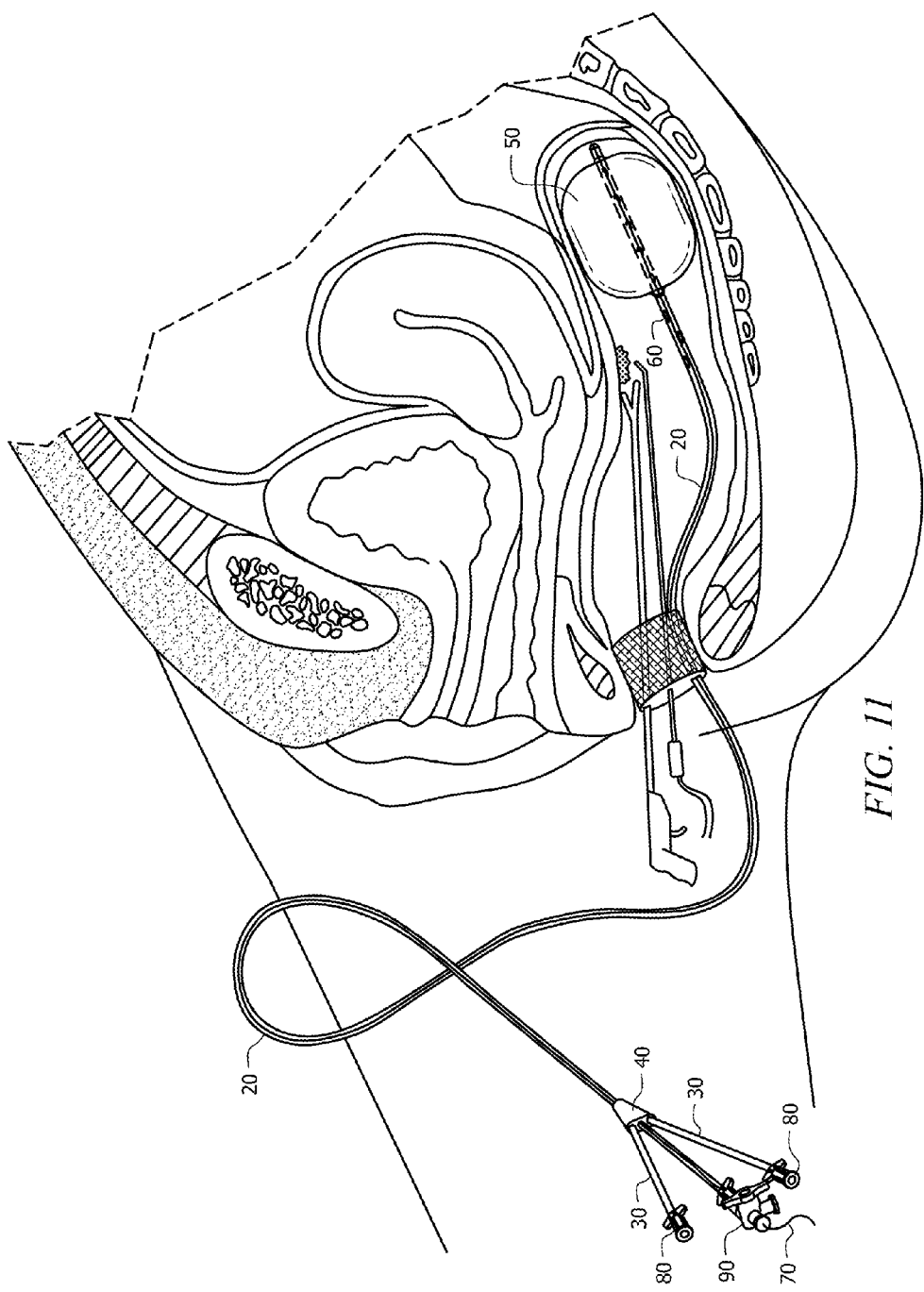
FIG. 11 is a cross sectional image of the intraluminal occluding catheter positioned for use in a woman's rectum.

In use, catheter 10 is capable of being inserted and guided into position within a physiological lumen such as the bowel. FIG. 11 illustrates catheter 10 in use in the rectum of a patient. While use in the rectum is illustrated, catheter 10 is capable of use in any endoscopic procedure and can be used to occlude any cavity such as the esophagus, small intestine, colon, or stomach. As shown in FIG. 11, a port is positioned within the opening of the physiological lumen, in this case, the port is inserted into the anus. There is a cap to the outside of the port to close the lumen off distally while the balloon closes the lumen proximally. The distal end (intraluminal end) of catheter 10 is inserted into the bowel through the port and positioned within the bowel proximal to the lesion or at the rectosigmoid junction. Once catheter 10 is positioned within the bowel, wire 70 may be removed and inflation of the balloon may be performed using a variety of methods such as, but not limited to, a syringe attached to one channel 30. Full occlusion of the bowel is assured by cessation of flow from the laparoscopic insufflator at an appropriate pressure. One channel 30 of the catheter 10 may have an endoscopic light extended therethrough to illuminate the visual field. Once occluded, the physician may excise the lesion and any smoke/vapor that may impair the visual field can be removed through another channel 30 in the catheter 10 by passive flow or with the use of a smoke removal system that is attached to external channel 30 by adaptor 80 or flow control device 90.

Successful maintenance of pneumorectum using balloon occlusion and lessening of the smoke or vapor produced using electrosurgical dissection in conjunction with removal of gas using the intraluminal catheter presented herein both allow for an obvious improvement in visualization and precision and along with facilitation of rectal defect closure may decrease total operative times. Better visualization, improved precision, decreased operative time, and lessened blood loss all improve surgical efficiency, safety, and post-operative outcomes.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described.

What is claimed is:

1. An intraluminal occluding catheter for prevention of loss of insufflation comprising:
 a catheter shaft comprising
  an exterior surface;
  an interior surface defining a single, undivided inner lumen;
  a distal section terminating at an intraluminal end;
  a plurality of orifices disposed in the distal section of the catheter shaft; and
  a proximal section terminating at an external end;
 a flexible balloon affixed to the intraluminal end wherein the intraluminal end of the catheter extends through an inner lumen of the flexible balloon whereby the flexible balloon is capable of conforming to a size and shape of a physiological lumen when filled with gas or fluid;
 a plurality of independent channels each having a proximal end, a distal end, and a wall extending between the proximal and distal ends wherein the plurality of independent channels extend through the single, undivided inner lumen of the catheter shaft and positioned adjacent to each other within the single, inner lumen of the catheter shaft;
 a sleeve attached to the external end of the catheter shaft wherein the plurality of independent channels extend through a proximal end of the sleeve and into the single, undivided inner lumen of the catheter shaft wherein the sleeve is tapered from the proximal end to a distal end of the sleeve;
 a flow control device positioned at the proximal end of each of the plurality of independent channels wherein the flow control device is a valve or a stopcock; and
 an insufflator attached to the flow control device of one independent channel of the plurality of independent channels;
 wherein the distal end of each channel has at least one aperture disposed along a circumference of the wall of the corresponding channel therein;
 wherein each aperture is substantially aligned with a corresponding orifice in a circumference of the catheter shaft;
 wherein the at least one aperture of a first independent channel of the plurality of independent channels and the corresponding orifice in the circumference of the catheter shaft is disposed within the flexible balloon;
 wherein the at least one aperture of a second independent channel of the plurality of independent channels and the corresponding orifice in the circumference of the catheter shaft is disposed immediately proximal to, but outside of, the flexible balloon; and
 wherein the at least one aperture of a third independent channel of the plurality of independent channels and the corresponding orifice in the circumference of the catheter shaft is disposed proximal to the at least one aperture of the second channel and thus farther from the flexible balloon.

2. The catheter of claim 1, further comprising an adapter positioned between the flow control device and the proximal end of each channel.

3. The catheter of claim 1, wherein the plurality of independent channels extend through the entire length of the single, undivided inner lumen of the catheter shaft from the external end to the intraluminal end.

4. The catheter of claim 3, further comprising a removable wire inserted into one of the plurality of independent channels to provide rigidity when inserting the catheter into a patient.

5. The catheter of claim 1, wherein the physiological lumen is selected from the group consisting of bowel, stomach, intestines, colon and esophagus.

6. An intraluminal occluding catheter for prevention of loss of insufflation comprising:

a catheter shaft having a distal section terminating in a closed intraluminal end, a proximal section, and a single, undivided inner lumen;

a plurality of orifices disposed in the distal section of the catheter shaft;

a flexible balloon affixed to the intraluminal end whereby the flexible balloon is capable of conforming to a size and shape of a physiological lumen when filled with gas or liquid;

a plurality of independent channels each having a distal end, a proximal end, and a wall extending between the distal end and the proximal end of the channel wherein the distal end of the plurality of independent channels extends through the single, undivided inner lumen from the proximal section to the distal section of the catheter shaft and positioned adjacent to each other within the single, undivided inner lumen of the catheter shaft;

an adapter for each channel having opposing ends, wherein one end of the opposing ends of each adapter is positioned at the proximal end of each respective channel;

a sleeve attached to an external end of the catheter shaft wherein the plurality of independent channels extend through a proximal end of the sleeve and into the single, undivided inner lumen of the catheter shaft wherein the sleeve is tapered from the proximal end to a distal end of the sleeve;

a flow control device positioned at the opposing end of the adapter of each channel, wherein the flow control device is a valve or a stopcock;

a smoke removal device attached to the flow control device of one of the plurality of independent channels; and an insufflator attached to the flow control device of another one of the plurality of independent channels;

wherein the distal end of each channel has at least one aperture disposed along a circumference of the wall of the corresponding channel therein;

wherein each aperture is substantially aligned with a corresponding orifice in a circumference of the catheter shaft;

wherein the at least one aperture of a first independent channel of the plurality of independent channels and the corresponding orifice in the circumference of the catheter shaft is disposed within the flexible balloon;

wherein the at least one aperture of a second independent channel of the plurality of independent channels and the corresponding orifice in the circumference of the catheter shaft is disposed immediately proximal to, but outside of, the flexible balloon;

wherein the at least one aperture of a third independent channel of the plurality of independent channels and the corresponding orifice in the circumference of the catheter shaft is disposed proximal to the at least one aperture of the second channel and thus farther from the flexible balloon; and wherein the smoke removal device is attached to one of the second independent channel and the third independent channel, and the insufflator is attached to the other one of the second independent channel and the third independent channel.

7. The catheter of claim 6, further comprising a removable wire inserted into one of the plurality of independent channels to provide rigidity when inserting the catheter into a patient.

8. The catheter of claim 6, wherein the physiological lumen is selected from the group consisting of bowel, stomach, intestines, colon and esophagus.

9. A method of preventing the loss of gas insufflation in a physiological lumen during a medical procedure comprising:

inserting an intraluminal occluding catheter for prevention of loss of insufflation into the physiological lumen, the intraluminal occluding catheter comprising:

a catheter shaft having a distal section terminating in a closed intraluminal end, a proximal section, and a single, undivided inner lumen;

a plurality of orifices disposed in the distal section of the catheter shaft:

a flexible balloon affixed to the intraluminal end whereby the flexible balloon is capable of conforming to a size and shape of a physiological lumen when filled with gas or liquid;

a plurality of independent channels each having a distal end, a proximal end, and a wall extending between the distal end and the proximal end of the channel wherein the distal end of the plurality of independent channels extends through the single, undivided inner lumen from the proximal section to the distal section of the catheter shaft and positioned adjacent to each other within the single, undivided inner lumen of the catheter shaft;

an adapter for each channel having opposing ends, wherein one end of the opposing ends of each adapter is positioned at the proximal end of each respective channel;

a sleeve attached to the an external end of the catheter shaft wherein the plurality of independent channels extend through a proximal end of the sleeve and into the single, undivided inner lumen of the catheter shaft wherein the sleeve is tapered from the proximal end to a distal end of the sleeve;

a flow control device positioned at the opposing end of the adapter of each channel, wherein the flow control device is a valve or a stopcock;

a smoke removal device attached to the flow control device of one of the plurality of independent channels; and an insufflator attached to the flow control device of another one of the plurality of independent channels;

wherein the distal end of each channel has at least one aperture disposed along a the circumference of the wall of the corresponding channel therein;

wherein each aperture is substantially aligned with a corresponding orifice in a circumference of the catheter shaft;

wherein the at least one aperture of a first independent channel of the plurality of independent channels and the corresponding orifice in the circumference of the catheter shaft is disposed within the flexible balloon;

wherein the at least one aperture of a second independent channel of the plurality of independent channels and the corresponding orifice in the circumference of the catheter shaft is disposed immediately proximal to, but outside of, the flexible balloon;

wherein the at least one aperture of a third independent channel of the plurality of independent channels and the corresponding orifice in the circumference of the catheter shaft is disposed proximal to the at least one aperture of the second channel and thus farther from the flexible balloon; and wherein the smoke removal device is attached to one of the second independent channel and the third independent channel, and the insufflator is attached to the other one of the second independent channel and the third independent channel;

inflating the flexible balloon to occlude the physiological lumen;

performing the medical procedure;

deflating the flexible balloon; and removing the intraluminal occluding catheter from the physiological lumen.

10. The method of claim 9, further comprising removing smoke or vapor produced by the medical procedure by allowing passive flow of gas through the corresponding orifices in the catheter shaft aligned with the at least one apertures of the second independent channel or the third independent channel.

11. The method of claim 9, further comprising removing smoke or vapor produced by the medical procedure by attaching the smoke removal device to the flow control device of the second independent channel or the third independent channel.

12. The method of claim 9, wherein the intraluminal occluding catheter is further comprised of a removable wire and wherein the method further comprising inserting the wire into one of the plurality of independent channels.

13. The method of claim 12, further comprising removing the wire from the channel after the intraluminal occluding catheter is inserted into the physiological lumen.

* * * * *